(12) United States Patent
Williams

(10) Patent No.: US 6,305,937 B1
(45) Date of Patent: Oct. 23, 2001

(54) RELEASABLY MOUNTABLE HAND GRIP FOR A DENTAL TOOL

(76) Inventor: Sharon L. Williams, 1930 North 7$^{th}$ St., Coeur d'Alene, ID (US) 83814

( * ) Notice: Subject to any disclaimer, the term of this patent is extended or adjusted under 35 U.S.C. 154(b) by 0 days.

(21) Appl. No.: 09/591,010

(22) Filed: Jun. 9, 2000

Related U.S. Application Data

(60) Provisional application No. 60/138,530, filed on Jun. 10, 1999.

(51) Int. Cl.$^7$ ........................................................ A61C 3/00
(52) U.S. Cl. ............................................ 433/141; 433/116
(58) Field of Search ...................... 433/102, 116, 433/141, 142, 143, 144, 145, 146, 147, 148, 149, 150, 151, 152, 153, 154, 155, 156, 157, 158, 159, 160, 161, 162, 163, 164

(56) References Cited

U.S. PATENT DOCUMENTS

| | | | |
|---|---|---|---|
| 2,073,137 | * | 3/1937 | Bimrose .............................. 433/116 |
| 4,721,021 | * | 1/1988 | Kusznir ................................. 81/489 |
| 5,501,597 | * | 3/1996 | Wilson ................................. 433/141 |
| 5,516,287 | * | 5/1996 | Zdarsky ............................... 433/141 |
| 5,775,346 | * | 7/1998 | Szyszkowski ....................... 433/142 |

* cited by examiner

Primary Examiner—John J. Wilson

(57) ABSTRACT

A releasably mountable hand grip (10) for a dental tool is installable on any tool, but is particularly adapted for installation on dental, dental hygiene and medical tools having a narrow cylindrical grip. A preferred version of the hand grip includes a generally cylindrical body (20) having a tapered front portion (25). A generally cylindrical channel (23) is oriented in a lengthwise manner along the axis of the body. The dimensions of the channel are incrementally greater than the outside dimensions of the tool onto which the grip may be installed. A plurality of ribs (30) are defined on the outside surface of the grip, and allow a frictional, slip-free connection to the finger tips of the user. The increase in the tools diameter due to the addition of the grip, the soft and flexible material from which the grip is made, and the frictional ribbed surface all contribute to a reduction in fatigue by the user.

3 Claims, 2 Drawing Sheets

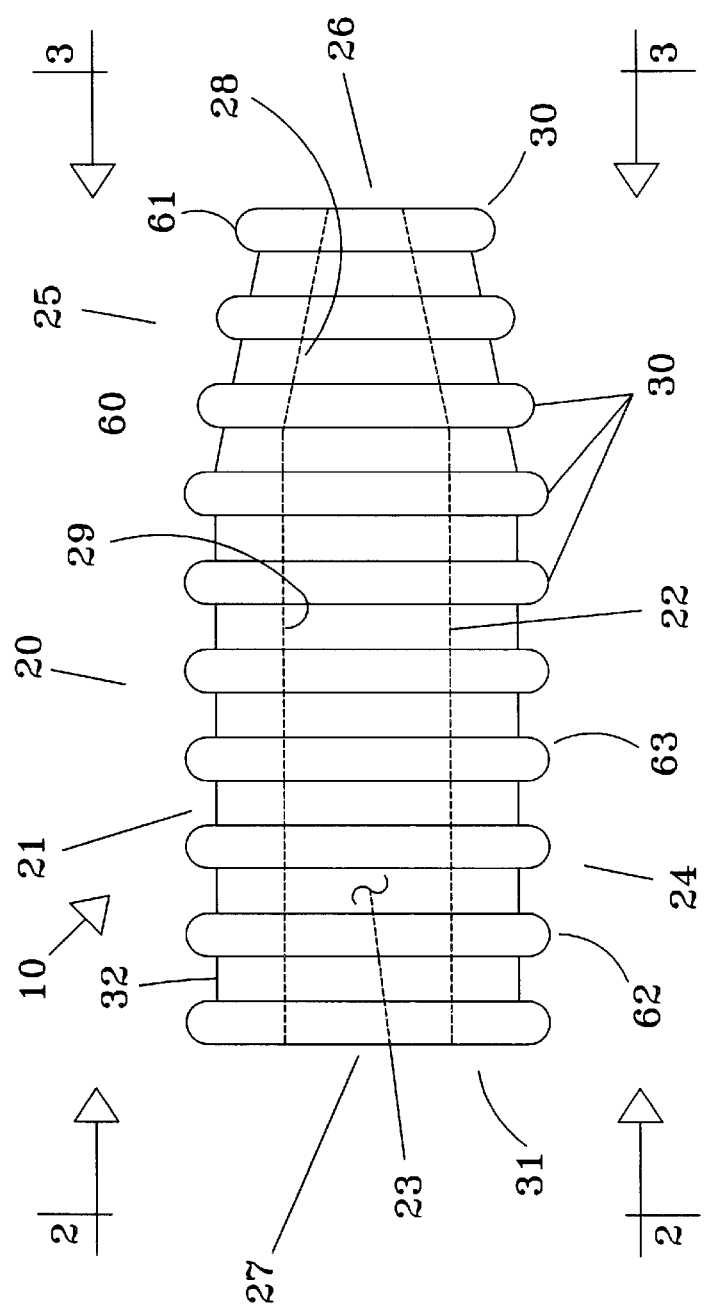
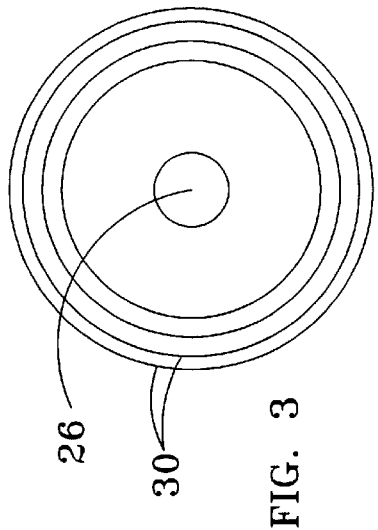
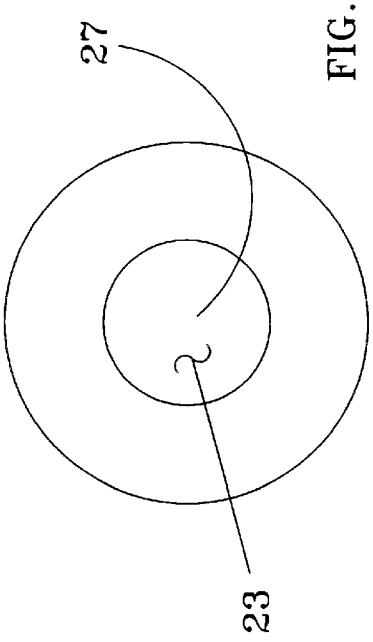
FIG. 1
FIG. 2
FIG. 3

RELEASABLY MOUNTABLE HAND GRIP FOR A DENTAL TOOL

CROSS-REFERENCES

This application claims the benefit of a provisional application filed Jan. 10, 1999 having serial No. 60/138,530.

BACKGROUND

It is well-known that repetitive motion by the wrist, hand and fingers can lead to adverse medical conditions such as carpal tunnel syndrome. In certain professions, the problem is particularly related to the size, shape and nature of the tool used, as well as the repetitive movements made with the tools. In the dental and dental hygiene professions, the extensive use of a number of small finger-gripped tools and instruments results in considerable hand fatigue. Over time, the hand fatigue may result in long-term or permanent injury.

One reason for the fatigue is the diameter of the tools used. Particularly where the diameter is quite small, the user's hand and fingers are additionally stressed. It is generally the case that hand fatigue increases when smaller diameter instruments are used, and decreases when larger diameter instruments are used.

Additionally, where the tool is made of a rigid material, such as steel, the user's hands and fingers must maintain a continuous position. Additional effort must typically be expended to maintain such a position over time.

And still further, where a tool is somewhat slippery due to small size and rigid construction, the tool may require still additional effort to control.

Nevertheless, in the dental, dental hygiene, other medical and non-medical fields there are a considerable number of tools which have been widely adopted and which therefore have a correspondingly large install base. Many of these tools are unlikely to be replaced in part due to the considerable expense involved, and in part due to their generally suitability for their associated task, with the exception of the fatigue and health issues of the user.

As a result, a solution to the above problems must be compatible with existing tools. For the foregoing reasons, there is a need for a releasable hand grip that can be retroactively added to dental, dental hygiene, medical and non-medical tools. The releasably mountable hand grip must significantly increase the diameter of the portion of the tool which is grasped, therefore making it more easily and comfortably handled. The grip must be made of a soft and non-rigid material, which is comfortable to the touch and which reduces stress and fatigue during use. The grip must be made with a non-slip textured surface which decreases the effort required to hold firmly to the tool. Additionally, the grip must be capable of being sterilized at very high temperatures without damage, and must be easily installed and removed from a tool.

SUMMARY

The present invention is directed to an apparatus that satisfies the above needs. A novel releasably mountable hand grip for a dental, dental hygiene, medical or non-medical tool is disclosed that can be retroactively added to such a tool, which increases the diameter of the portion of the tool which is grasped, which is made of a soft and non-rigid material with a non-slip textured surface, and which is capable of being sterilized at very high temperatures without damage.

A version of the releasably mountable hand grip for a dental tool of the present invention provides some or all of the following structures, and wherein a preferred version includes some or all of the following detailed dimensions.

(A) A generally cylindrical body 20 includes a cylindrical portion 24 0.86 inches long attached to a tapered front portion 25 0.64 inches long. The body has an inside surface 22 defining an axially oriented channel 23 1.5 inches long between a smaller front opening 26 having a radius of 0.07 inches defined in a first end 30 of the body and a larger rear opening 27 having a radius of 0.125 inches defined in a second end 31 of the body. The axially oriented channel has a cylindrical channel portion 29 0.86 inches long and a tapered channel portion 28 0.64 inches long.

(B) A plurality of ribs 60 includes six larger rear ribs 62 having an outside diameter of 0.5 inches carried by the cylindrical portion 24 and four smaller front ribs 61 having outside diameters of at least 0.32 inches carried by the tapered front portion 25. The plurality of ribs are defined on an outside surface 21 of the body and adjacent ribs are separated by a surface between ribs 32 resulting in a distance between ribs of 0.10 inches. Each of the plurality of ribs is defined within a plane that is perpendicular to a lengthwise axis traveling through the center of the body 20 resulting in a rib thickness of 0.06 inches.

(C) A preferred version of the invention is made of any of the well-known types of soft silicone compounds which are slightly compressible to the touch, resulting in a comfortable grip. A medical grade of rubber silicone is preferred. The material selected should be capable of being sterilized at very high temperatures, up to 600 degrees F. The material should be resistant to exposure to isopropyl alcohol, and should be made of a compound that can be color coded.

It is therefore a primary advantage of the present invention to provide a novel releasably mountable hand grip for a dental or other type tool that significantly increases the diameter of the portion of the tool grasped, thereby reducing the effort and fatigue associated with tool use.

Another advantage of the present invention is to provide a novel releasably mountable hand grip for a dental or other type tool having a non-slip surface defining a number of ribs which allow the user to control the movement and location of the tool, even when applying force which would otherwise tend to cause the tool to move against the user's grip.

A still further advantage of the present invention is to provide a novel releasably mountable hand grip for a dental or other type tool that is heat sterilizable, that can be color coded and that can be installed and removed with little effort and no difficulty.

DRAWINGS

These and other features, aspects, and advantages of the present invention will become better understood with regard to the following description, appended claims, and accompanying drawings where:

FIG. 1 is a side orthographic view of a version of the releasably mountable hand grip for a dental tool of the invention.

FIG. 2 is an end orthographic view of the hand grip of FIG. 1.

FIG. 3 is an end orthographic view taken from the opposite direction as that seen in FIG. 2.

DESCRIPTION

Figure 4:
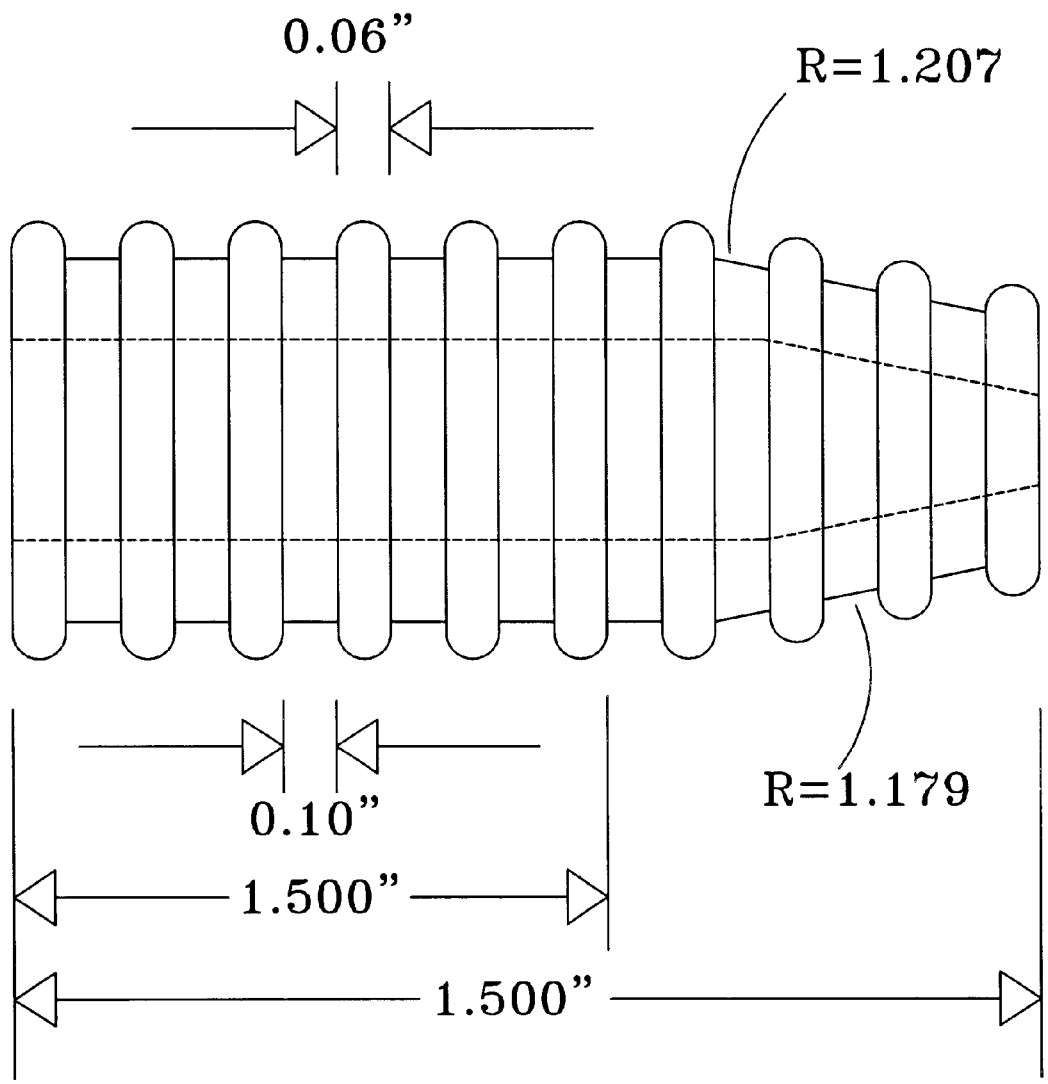
FIG. 4 is a dimensioned side orthographic view of the hand grip.
Figure 5:
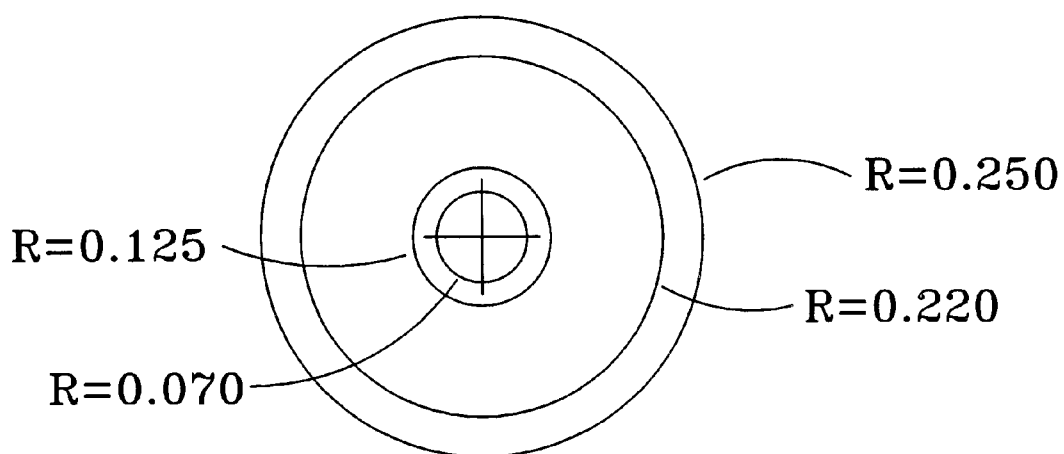
FIG. 5 is a dimensioned end orthographic view of the hand grip.

Referring in generally to FIGS. 1 through 5, a releasably mountable hand grip 10 for a dental tool constructed in accordance with the principles of the invention is seen. The releasable hand grip is installable on any tool, but is particularly adapted for installation on dental, dental hygiene and medical tools having a narrow cylindrical, six-sided or similar grip. A preferred version of the hand grip 10 includes a generally cylindrical body 20 having a tapered front portion 25. A generally cylindrical channel 23 is oriented in a lengthwise manner along the axis of the body. The dimensions of the channel are greater than the outside dimensions of the tool onto which the grip may be installed. A plurality of ribs 30 are defined on the outside surface of the grip, and allow a frictional, slip-free connection to the finger tips of the user. The increase in the tool's diameter due to the addition of the grip, the soft and flexible material from which the grip is made, and the frictional ribbed surface all contribute to a reduction in fatigue by the user.

As seen in the figures, the body 20 is generally cylindrical, having a cylindrical rear portion 24 and a tapered front portion 25. The outside surface 21 is covered by a pattern of ribs 60 which are spaced at regular intervals. The inside surface 22 defines a channel 23 which extends the length of the body between a small front opening 26 and a larger rear opening 27.

In a preferred embodiment with specific dimensions, the generally cylindrical body 20 includes a cylindrical portion 24 0.86 inches long and an attached tapered front portion 25 0.64 inches long. The body has an inside surface 22 defining an axially oriented channel 23 1.5 inches long between a smaller front opening 26 having a radius of 0.07 inches defined in a first end 30 of the body and a larger rear opening 27 having a radius of 0.125 inches defined in a second end 31 of the body. The axially oriented channel has a cylindrical channel portion 29 0.86 inches long and a tapered channel portion 28 0.64 inches long.

Continuing to refer to the dimensions of the preferred embodiment, a plurality of ribs 60 includes six larger rear ribs 62 having an outside diameter of 0.5 inches carried by the cylindrical portion 24 and four smaller front ribs 61 having outside diameters of at least 0.32 inches carried by the tapered front portion 25. The plurality of ribs are defined on an outside surface 21 of the body and adjacent ribs are separated by a surface 32 between ribs resulting in a distance between ribs of 0.10 inches. Each of the plurality of ribs is defined within a plane that is perpendicular to a lengthwise axis traveling through the center of the body 20 resulting in a rib thickness of 0.06 inches and a rounded corner 63.

A preferred body is made of soft, flexible yet resilient silicone rubber compound which provides a somewhat padded surface which is less fatiguing to grip over an extended period of time. The silicone compound should be selected to be extremely resistant to isopropyl alcohol. Such silicone compounds are slightly compressible to the touch, resulting in a comfortable grip. A medical grade of rubber silicone is preferred. The material selected should be capable of being sterilized at very high temperatures, up to 600 degrees F. The material should be resistant to exposure to isopropyl alcohol, and should be made of a compound that can be color coded.

The grip 10 can be manufactured in any size to fit any tool or application. However, in a preferred embodiment for dental hygiene applications, the body is approximately 1.5" long. The diameter of the channel is 0.290" at the large opening 27 and 0.140" at the small opening. The diameter of the of the outside surface 21 is 0.440" in the locations where there are no ribs along the cylindrical rear portion 24. The diameter of the ribs is 0.500" at the greatest, along the cylindrical rear portion 24. The diameter of the outside surface tapers to approximately 0.250" in the tapered front portion 25. The diameter of the forward most rib, adjacent to the small front opening 26, is 0.320". The distance between ribs, center to center, is 0.160". The radius of each rib is 0.029". In a preferred application, 10 ribs are present, including 6 larger rear ribs 62 and four smaller front ribs 61.

The material used in the manufacturing process should be sufficiently heat resistant to allow sterilization, and therefore reuse. It is typically the case that plastic is unable to withstand the heat of sterilization, and that therefore silicone or a silicone compound should be used. A preferred silicone compound should be heat-resistant to 600 degrees F. Such heat resistance allows the grip 10 to be sterilized along with the tool, allowing repeated reuse of the tool, making repeated removal and installation unnecessary.

To use the releasably mountable hand grip for a dental or other type tool, the user first installs the grip on the tool. Since the grip is resiliently deformable, the grip may be twisted and bent somewhat, to facilitate installation. This is particularly true where a hooked tip or scraper is present on the tool, requiring some twisting of the grip. If desired, a small amount of isopropyl alcohol may be used as a lubricant to aid in moving the hand grip over the tool. Once the grip is slipped over the end of the tool, it is slid rearwardly, until the diameter of the opening 26 is equal to the diameter of the tool, stopping movement of the grip. Due to the loose fit between the inside surface 22 of the channel 23 and the tool, there is some flexibility of the grip. This flexibility contributes to the comfort experienced by the user when operating the tool by holding the grip.

After use, the tool may be sterilized by heating, in a well-known manner. Due to the construction of the grip, the heat does not cause damage, and the grip may be reused.

To remove the grip, the user simply pulls on the grip, causing the tool to pass through the channel 23 and out the rear opening 27.

The previously described versions of the present invention have many advantages, including a primary advantage of providing a novel releasably mountable hand grip for a dental or other type tool that significantly increases the diameter of the portion of the tool grasped, thereby reducing the effort and fatigue associated with tool use.

Another advantage of the present invention is to provide a novel releasably mountable hand grip for a dental or other type tool having a non-slip surface defining a number of ribs which allow the user to control the movement and location of the tool, even when applying force which would otherwise tend to cause the tool to move against the user's grip.

A still further advantage of the present invention is to provide a novel releasably mountable hand grip for a dental or other type tool that is heat sterilizable, that can be color coded and that can be installed and removed with little effort and no difficulty.

Although the present invention has been described in considerable detail and with reference to certain preferred versions, other versions are possible. For example, while a preferred surface texture has been disclosed, having a number of ribs radially oriented about a lengthwise axis, it is clear that certain modifications could be made while still in keeping within the scope and teachings of the invention.

Therefore, the spirit and scope of the appended claims should not be limited to the description of the preferred versions disclosed.

In compliance with the U.S. Patent Laws, the invention has been described in language more or less specific as to methodical features. The invention is not, however, limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A releasably mountable hand grip for a dental tool, comprising:
   (A) a body comprising a cylindrical portion and an attached tapered front portion, the body having an inside surface defining an axially oriented channel between a smaller front opening defined in a first end of the body and a larger rear opening defined in a second end of the body, the axially oriented channel having a cylindrical portion and a tapered front portion; and
   (B) a plurality of ribs, comprising at least two larger rear ribs carried by the cylindrical portion and at least two smaller front ribs carried by the tapered front portion, wherein the plurality of ribs are defined on an outside surface of the body, each rib defined within a plane that is perpendicular to a lengthwise axis traveling through the center of the body; and
   (C) wherein the body is made of medical grade rubber silicone and is color coded.

2. A releasably mountable hand grip for a dental tool, comprising:
   (A) a body comprising a cylindrical portion and an attached tapered front portion, the body having an inside surface defining an axially oriented channel between a smaller front opening defined in a first end of the body and a larger rear opening defined in a second end of the body, the axially oriented channel having a cylindrical portion and a tapered front portion; and
   (B) a plurality of ribs, comprising six larger rear ribs carried by the cylindrical portion and four smaller front ribs carried by the tapered front portion, wherein the plurality of ribs are defined on an outside surface of the body and wherein adjacent ribs are separated by a surface between ribs, and wherein each of the plurality of ribs is defined within a plane that is perpendicular to a lengthwise axis traveling through the center of the body.

3. A releasably mountable hand grip for a dental tool, comprising:
   (A) a body comprising a cylindrical portion 0.86 inches long and an attached tapered front portion 0.64 inches long, the body having an inside surface defining an axially oriented channel 1.5 inches long between a smaller front opening having a radius of 0.07 inches defined in a first end of the body and a larger rear opening having a radius of 0.125 inches defined in a second end of the body, the axially oriented channel having a cylindrical portion 0.86 inches long and a tapered front portion 0.64 inches long;
   (B) a plurality of ribs, comprising six larger rear ribs having an outside diameter of 0.5 inches carried by the cylindrical portion and four smaller front ribs having outside diameters of at least 0.32 inches carried by the tapered front portion, wherein the plurality of ribs are defined on an outside surface of the body and wherein adjacent ribs are separated by a surface between ribs resulting in a distance between ribs of 0.10 inches, and wherein each of the plurality of ribs is defined within a plane that is perpendicular to a lengthwise axis traveling through the center of the body resulting in a rib thickness of 0.06 inches; and
   (C) wherein the body is made of medical grade rubber silicone and is color coded.

* * * * *